(12) United States Patent
Prescott

(10) Patent No.: US 8,433,590 B2
(45) Date of Patent: *Apr. 30, 2013

(54) SYSTEM AND METHOD FOR PROVIDING HEALTHCARE-RELATED SERVICES

(76) Inventor: Daniel J. Prescott, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/405,801

(22) Filed: Feb. 27, 2012

(65) Prior Publication Data

US 2012/0158438 A1    Jun. 21, 2012

Related U.S. Application Data

(63) Continuation of application No. 11/941,706, filed on Nov. 16, 2007, now Pat. No. 8,150,714.

(60) Provisional application No. 60/859,604, filed on Nov. 17, 2006.

(51) Int. Cl.
*G06Q 40/00* (2012.01)

(52) U.S. Cl.
USPC .............................................................. 705/4

(58) Field of Classification Search ........................ 705/4
See application file for complete search history.

(56) References Cited

U.S. PATENT DOCUMENTS

| | | | |
|---|---|---|---|
| 6,256,614 B1 | 7/2001 | Wecker et al. | |
| 7,305,347 B1 | 12/2007 | Joao | |
| 7,343,309 B2 | 3/2008 | Ogawa et al. | |
| 7,398,220 B1 | 7/2008 | Hayes | |
| 2002/0088851 A1 | 7/2002 | Hodes | |
| 2003/0219709 A1* | 11/2003 | Olenick et al. | 434/350 |
| 2004/0139318 A1* | 7/2004 | Fiala et al. | 713/165 |
| 2004/0148203 A1* | 7/2004 | Whitaker et al. | 705/4 |
| 2004/0186744 A1 | 9/2004 | Lux | |
| 2005/0187790 A1 | 8/2005 | Lapsker | |
| 2005/0187793 A1 | 8/2005 | Myles | |
| 2006/0069619 A1 | 3/2006 | Walker et al. | |
| 2007/0051797 A1 | 3/2007 | Randolph-Wall et al. | |
| 2007/0162307 A1 | 7/2007 | Austin et al. | |
| 2008/0059251 A1 | 3/2008 | Biorge | |
| 2008/0120145 A1 | 5/2008 | Prescott | |
| 2008/0126140 A1 | 5/2008 | Sutton | |
| 2008/0147441 A1 | 6/2008 | Kil | |
| 2008/0154650 A1 | 6/2008 | Matisonn et al. | |

OTHER PUBLICATIONS

U.S. Appl. No. 60/859,604, filed Nov. 17, 2006, Prescott.
Office Action, mailed May 11, 2010, by the USPTO regarding U.S. Appl. No. 11/941,706.
Interview Summary, mailed Aug. 18, 2010, by the USPTO regarding U.S. Appl. No. 11/941,706.
Office Action, mailed Oct. 27, 2010, by the USPTO regarding U.S. Appl. No. 11/941,706.

(Continued)

*Primary Examiner* — Hani M Kazimi
*Assistant Examiner* — Hatem M Ali
(74) *Attorney, Agent, or Firm* — Haynes and Boone, LLP

(57) ABSTRACT

A system and method for providing healthcare-related services according to which the healthcare-related services include, but are not limited to, health insurance benefit activation services and/or healthcare-related education services.

6 Claims, 10 Drawing Sheets

OTHER PUBLICATIONS

Office Action, mailed Feb. 15, 2011, by the USPTO regarding U.S. Appl. No. 11/941,706.
Interview Summary, mailed Apr. 21, 2011, by the USPTO regarding U.S. Appl. No. 11/941,706.
Final Office Action, mailed Jul. 19, 2011, by the USPTO regarding U.S. Appl. No. 11/941,706.
Notice of Allowance, mailed Nov. 23, 2011, by the USPTO regarding U.S. Appl. No. 11/941,706.
Chad Previch and Tony Thornton; Calling-card prizes raise legal questions; Knight Rider Tribune Business News. Washington: Oct 19, 2005. p. 1.
A Report card for health care; [Chicago Edition] Chicago Tribune. Chicago, Ill.: Jul. 11, 2007. p. 20.
Linda Lloyd. Area firms test 'smart cards' N.Y. patients; Knight Rider Tribune Business News. Washington: Jun 18, 2007. p. 1.

* cited by examiner

| SERVICES | BENEFIT | RESULTS | OFFERING | MEASUREMENT |
|---|---|---|---|---|
| ACTIVATION OF HEALTH INSURANCE BENEFIT | ENSURES EACH CLIENT AND SPOUSE USES HEALTH INSURANCE BENEFIT EFFECTIVELY | BETTER UTILIZATION AND DECREASED UNNECESSARY CLAIM EXPENSES | GUARANTEE 98% OF CLIENTS AND SPOUSES ARE EDUCATED CONSUMERS | PROVIDE ACTIVATION REPORTS |
| CLIENT HEALTH PROFILE | CLIENT-TARGETED PREVENTATION PROGRAMS AND ACCURACY OF DATA | IMPROVED HEALTHCARE PREDICTION MODELS; DECREASED COSTS AND PREMIUMS | OBTAIN CLIENT HEALTH DATA AND CATEGORIZE HEALTH RISKS | SHRINKING DISEASE MANAGEMENT GROUP; MID-YEAR / YEAR-OVER-YEAR BEHAVIOR CHANGES |
| HEALTHCARE-RELATED EDUCATION SERVICES: GENERIC DRUG EDUCATION | KNOW WHO TO USE FOR DOCTOR VISITS | "JUST ASK" THE DOCTOR AND SWITCH TO GENERIC DRUGS; DECREASED COSTS AND PREMIUMS | EDUCATE ON COST, AND GENERIC EQUIVALENTS | HEALTH INSURANCE COMPANY DRUG COSTS AND COUPON EXECUTIONS |
| HEALTH EDUCATION | DELIVER TARGETED EDUCATION BASSED ON CLIENT HEALTH PROFILES | HEALTHY LIFESTYLES; DECREASED COSTS AND PREMIUMS | QUARTERLY EDUCATION MATERIAL DELIVERED, AND SPECIFIC, TO CLIENT HEALTH PROFILE AND SEASONALITY ISSUES | SHRINKING DISEASE MANAGEMENT GROUP; MID-YEAR / YEAR-OVER-YEAR BEHAVIOR CHANGES |
| HEALTHCARE-RELATED MARKETING SERVICES: HEALTH INSURANCE COMPANY BRANDING | INCRASE BRAND LOYALTY AMONG CLIENTS | INCREASE REPEAT BUSINESS | DELIVER HEALTH-INITIATIVE SPECIFIC PROMOTIONAL PRODUCTS | YEAR-END CUSTOMER SURVEYS |
| CLIENT RESEARCH | OBTAIN CLIENT PREFERENCE AND MARKET DATA | TARGETED CLIENT INPUT | PERFORM CUSTOMIZED QUESTIONNAIRE | CUSTOMIZED MARKET DATA REPORTS |

FIG. 8

| SERVICES | ACTIVATION & BASIC EDUCATION | ACTIVATION, ADVANCED EDUCATION & PREVENTION | ACTIVATION, ADVANCED EDUCATION, PREVENTION & ASSESSMENT |
|---|---|---|---|
| ACTIVATION OF HEALTH INSURANCE BENEFIT | ✓ | ✓ | ✓ |
| HEALTHCARE & PRESCRIPTION DRUG EDUCATION | ✓ | ✓ | ✓ |
| HSA / HRA EDUCATION | ✓ | ✓ | ✓ |
| ACTIVATION REPORT | ✓ | ✓ | ✓ |
| MID-YEAR HEALTHY HABITS TELEPHONE CALL | ✓ | ✓ | ✓ |
| WEBSITE TRAFFIC INCENTIVE | ✓ | ✓ | ✓ |
| CLIENT RISK ASSESSMENT PROFILE | | ✓ | ✓ |
| AT-RISK & PREVENTION EDUCATION | | ✓ | ✓ |
| GENERIC/OVER-THE-COUNTER INCENTIVES | | ✓ | ✓ |
| BRAND LOYALTY PROGRAMS | | ✓ | ✓ |
| CUSTOMIZED CLIENT SURVEY | | | ✓ |
| PREMIUM BRAND GIFTS | | | ✓ |
| PROGRAM RESPONSE REPORTS | | | ✓ |
| | | | |
| COST / ADULT / MONTH | $ 2 | $ 3 | $ 4 |

FIG. 9

SYSTEM AND METHOD FOR PROVIDING HEALTHCARE-RELATED SERVICES

CROSS REFERENCE TO RELATED APPLICATION

This application is a continuation of U.S. application Ser. No. 11/941,706, filed Nov. 16, 2007, which claims the benefit of the filing date of U.S. application No. 60/859,604, filed on Nov. 17, 2006, the disclosures of which are incorporated herein by reference.

BACKGROUND

The present disclosure relates in general to healthcare, and in particular to a system and method for providing healthcare-related services, including, but not limited to, health insurance benefit activation services and/or healthcare-related education services.

BRIEF DESCRIPTION OF THE DRAWINGS

FIG. 8 is a table outlining services, benefits, results, offerings and measurements of the system of FIGS. 1, 2, 3A and 3B, and/or the method of FIGS. 5, 6 and 7, according to several exemplary embodiments.

FIG. 9 is a table outlining packages and programs available using the system of FIGS. 1, 2, 3A and 3B, and/or the method of FIGS. 5, 6 and 7, according to several exemplary embodiments.

DETAILED DESCRIPTION

Figure 1:
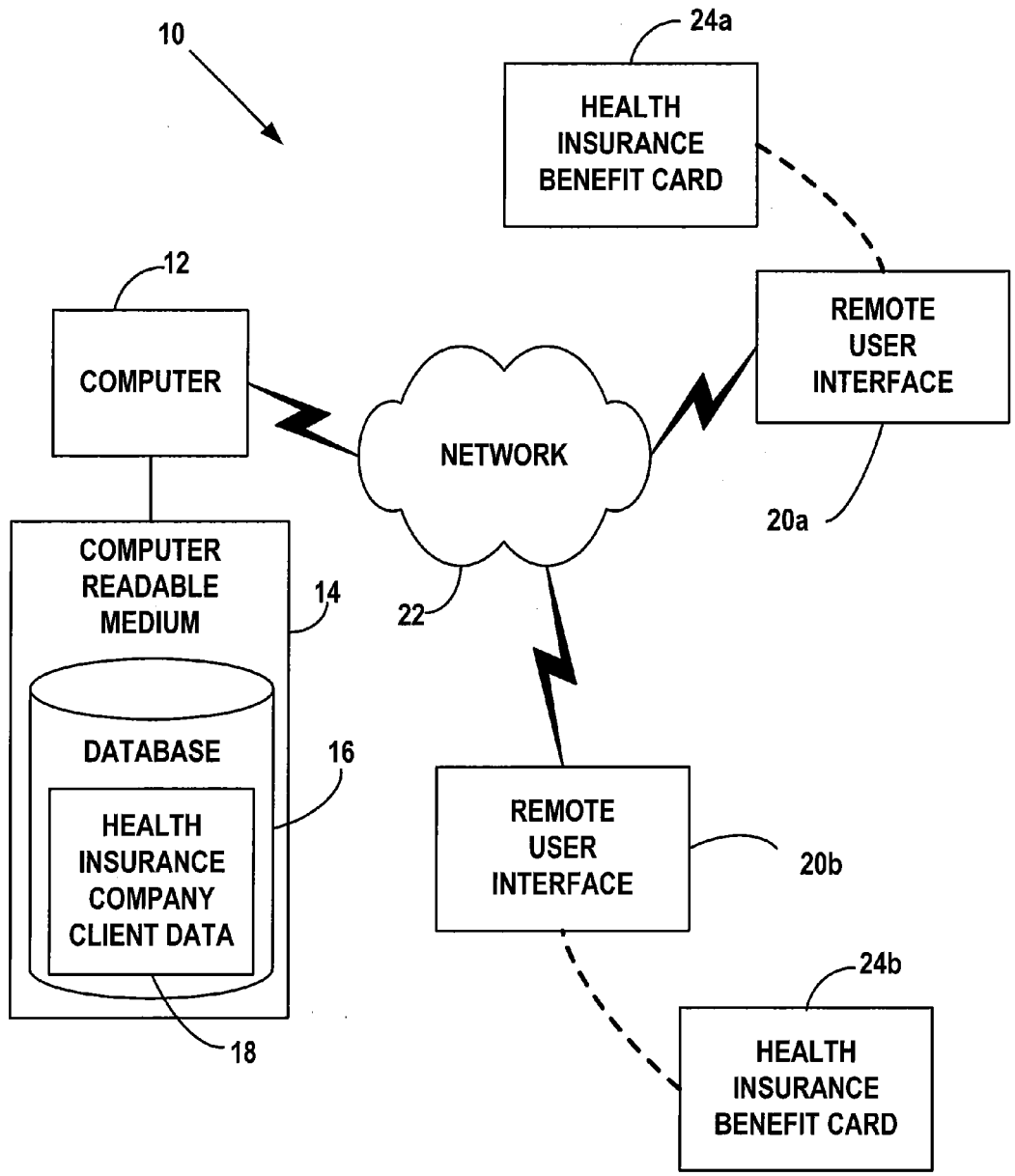
FIG. 1 is a diagrammatic illustration of a system according to an exemplary embodiment, the system including a plurality of health insurance benefit cards, a plurality of remote user interfaces, a computer, a computer readable medium and a database including health insurance company client data.

In an exemplary embodiment, as illustrated in FIG. 1, a system for providing healthcare-related services is generally referred to by the reference numeral 10 and includes a computer 12 and a computer readable medium 14 operably coupled thereto. Instructions accessible to, and executable by, the computer 12 are stored in the computer readable medium 14. A database 16, including heath insurance company client data 18, is also stored in the computer readable medium 14. Remote user interfaces 20a and 20b are operably coupled to the computer 12 via a network 22. In several exemplary embodiments, the network 22 includes the Internet, any type of local area network, any type of wide area network, any type of wireless network, any type of data network, any type of voice network, any type of telephone network, and/or any combination thereof. In several exemplary embodiments, each of the remote user interfaces 20a and 20b includes a telephone, a personal computer, a personal digital assistant, a cellular telephone, other types of telecommunications devices, other types of computing devices, and/or any combination thereof.

Health insurance benefit cards 24a and 24b are associated with the remote user interfaces 20a and 20b, respectively. In an exemplary embodiment, each of the benefit cards 24a and 24b evidences a health insurance benefit. In an exemplary embodiment, each of the benefit cards 24a and 24b is a wallet-sized plastic card, a letter, a postcard, and/or any combination thereof. In an exemplary embodiment, the benefit cards 24a and 24b are positionally associated with, or in the vicinity of, the remote user interfaces 20a and 20b, respectively. In an exemplary embodiment, each of the benefit cards 24a and 24b is the content of an e-mail message. In an exemplary embodiment, the benefit cards 24a and 24b are electronically associated with, or electronically stored in, the remote user interfaces 20a and 20b, respectively.

In several exemplary embodiments, instead of, or in addition to the database 16, the computer readable medium 14 includes one or more other databases and/or one or more data structures stored therein. In several exemplary embodiments, the computer 12 includes, and/or is operably coupled to, one or more communication modules and/or devices.

Figure 2:
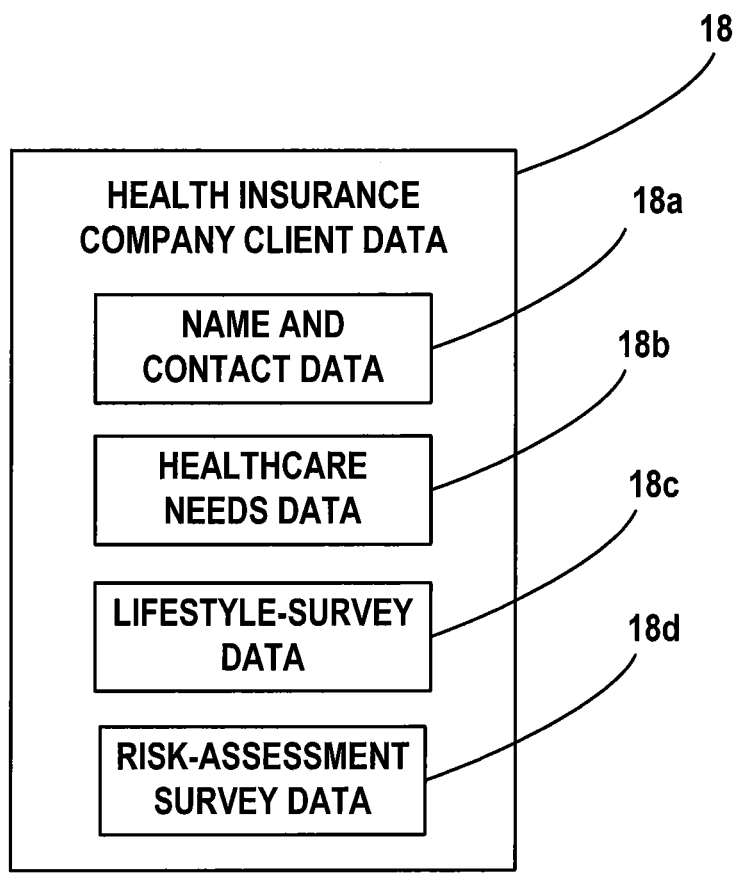
FIG. 2 is a diagrammatic illustration of the health insurance company client data of FIG. 1 according to an exemplary embodiment.

In an exemplary embodiment, as illustrated in FIG. 2 with continuing reference to FIG. 1, the health insurance company client data 18 includes data specific to a member, customer or client of a health insurance company, namely name and contact data 18a, healthcare needs data 18b, lifestyle survey data 18c and risk-assessment survey data 18d. In an exemplary embodiment, the name and contact data 18a includes, for example, one or more of the client's name, spouse's name, dependents' names, residence address, post office address, home telephone number, work telephone number, facsimile number, home or personal e-mail address, and/or work e-mail address. In an exemplary embodiment, the healthcare needs data 18b includes any data documenting, listing and/or describing any healthcare needs specific to the client. In an exemplary embodiment, the lifestyle survey data 18c includes any data documenting, listing and/or describing the lifestyle of the client as it relates to the health of the client. In an exemplary embodiment, the risk-assessment survey data 18d includes any data documenting, listing and/or describing any health-related risks specific to the client. In several exemplary embodiments, one or more of the data 18a, 18b, 18c and 18d may be combined, shared and/or based on one or more of the other of the data 18a, 18b, 18c and 18d.

Figure 3A:
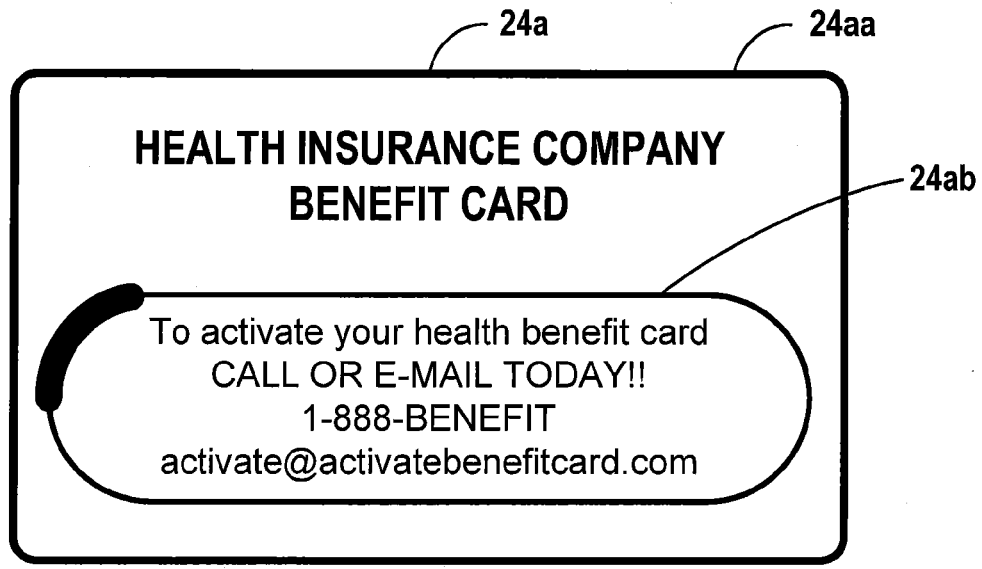
FIG. 3A is a front elevational view of one of the health insurance benefit cards of FIG. 1 according to an exemplary embodiment.

In an exemplary embodiment, as illustrated in FIG. 3A with continuing reference to FIGS. 1 and 2, the benefit card 24a includes a wallet-sized plastic card 24aa having a removable tag or label, such as a peel-off label 24ab, coupled thereto. The label 24ab includes a message instructing the holder of the card 24a to call a telephone number shown on the label 24*ab*, or to send an e-mail message to an e-mail address shown on the label 24*ab*. In several exemplary embodiments, the messages on the label 24*ab* may be printed in one or more languages.

Figure 3B:
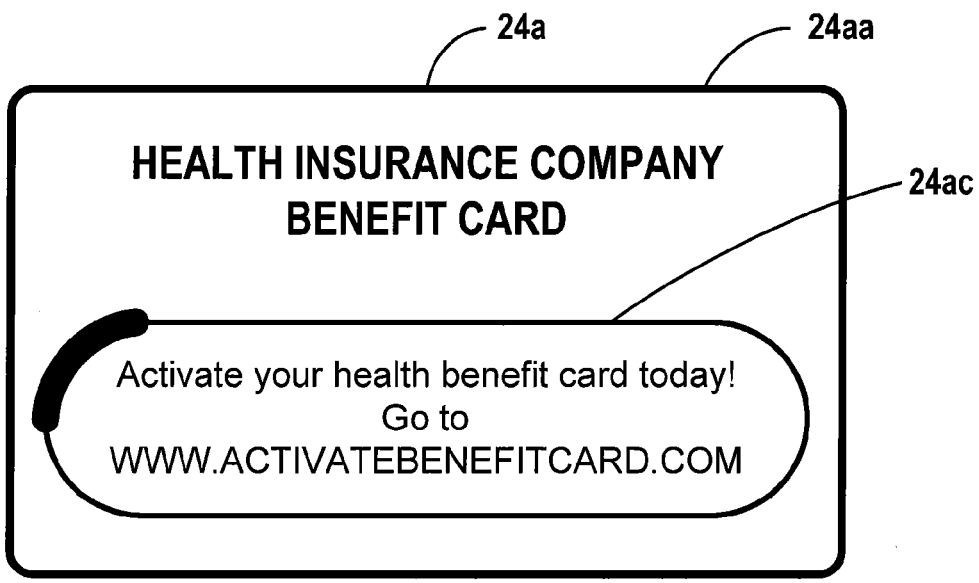
FIG. 3B is a front elevational view of one of the health insurance benefit cards of FIG. 1 according to another exemplary embodiment.

In an exemplary embodiment, as illustrated in FIG. 3B with continuing reference to FIGS. 1, 2 and 3A, the benefit card 24*a* includes the wallet-sized plastic card 24*aa* having a removable tag or label, such as a peel-off label 24*ac*, coupled thereto, instead of, or in addition to the label 24*ab*. The label 24*ac* includes a message instructing the holder of the card 24*a* to access a website using the domain name shown on the label 24*ac*. In several exemplary embodiments, the messages on the label 24*ac* may be printed in one or more languages.

In an exemplary embodiment, the benefit card 24*b* is substantially similar to the benefit card 24*a* and therefore will not be described in detail.

Figure 4:
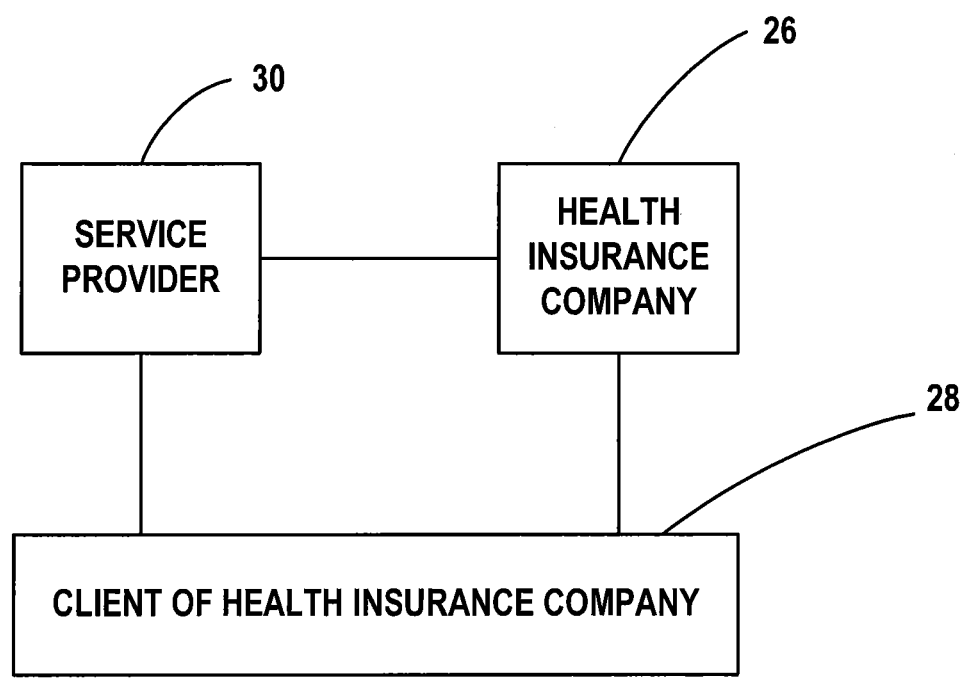
FIG. 4 is a diagrammatic illustration of persons and/or entities associated with the system of FIG. 1 according to an exemplary embodiment, including a health insurance company, a client of the health insurance company, and a service provider.

In an exemplary embodiment, as illustrated in FIG. 4 with continuing reference to FIGS. 1, 2, 3A and 3B, the operation of the system 10, which is described below, involves a health insurance company 26, and a consumer, member, customer or client 28 of the health insurance company 26. In an exemplary embodiment, the client 28 is a client of the health insurance company 26 by virtue of the client 28 being an employee of an entity or organization with which the health insurance company 26 has an agreement to provide health insurance to the organization's employees. In an exemplary embodiment, the client 28 is a client of the health insurance company 26 by virtue of an agreement between the client 28 and the health insurance company 26. A service provider 30 provides services to the client 28 on behalf of the health insurance company 26, and further provides services to the health insurance company 26. In several exemplary embodiments, the service provider 30 has an agreement with the health insurance company 26 which outlines the scope of the services provided to the client 28, and to the health insurance company 26, which services are described in further detail below. In an exemplary embodiment, the service provider 30 is an entity which is independent of the health insurance company 26. In an exemplary embodiment, the service provider 30 is a subsidiary, or is part, of the health insurance company 26. In an exemplary embodiment, the service provider 30 and the health insurance company 26 are the same company. In several exemplary embodiments, the health insurance company 26 has a plurality of members, customers or clients, including clients who are spouses of other clients, each of which will be referred to using the reference numeral 28. In an exemplary embodiment, the health insurance company 26 is an entity or organization whose primary business or businesses are unrelated to providing health insurance, but is self insured as to health insurance. In an exemplary embodiment, the health insurance company 26 is an entity or organization of which the client 28 is an employee, or with which the client 28 is otherwise affiliated, and, although the primary business or businesses of the entity or organization are unrelated to health insurance, the entity or organization is self insured, and thus directly provides health insurance to the client 28, instead of using a third party to provide health insurance to the client 28.

Figure 5:
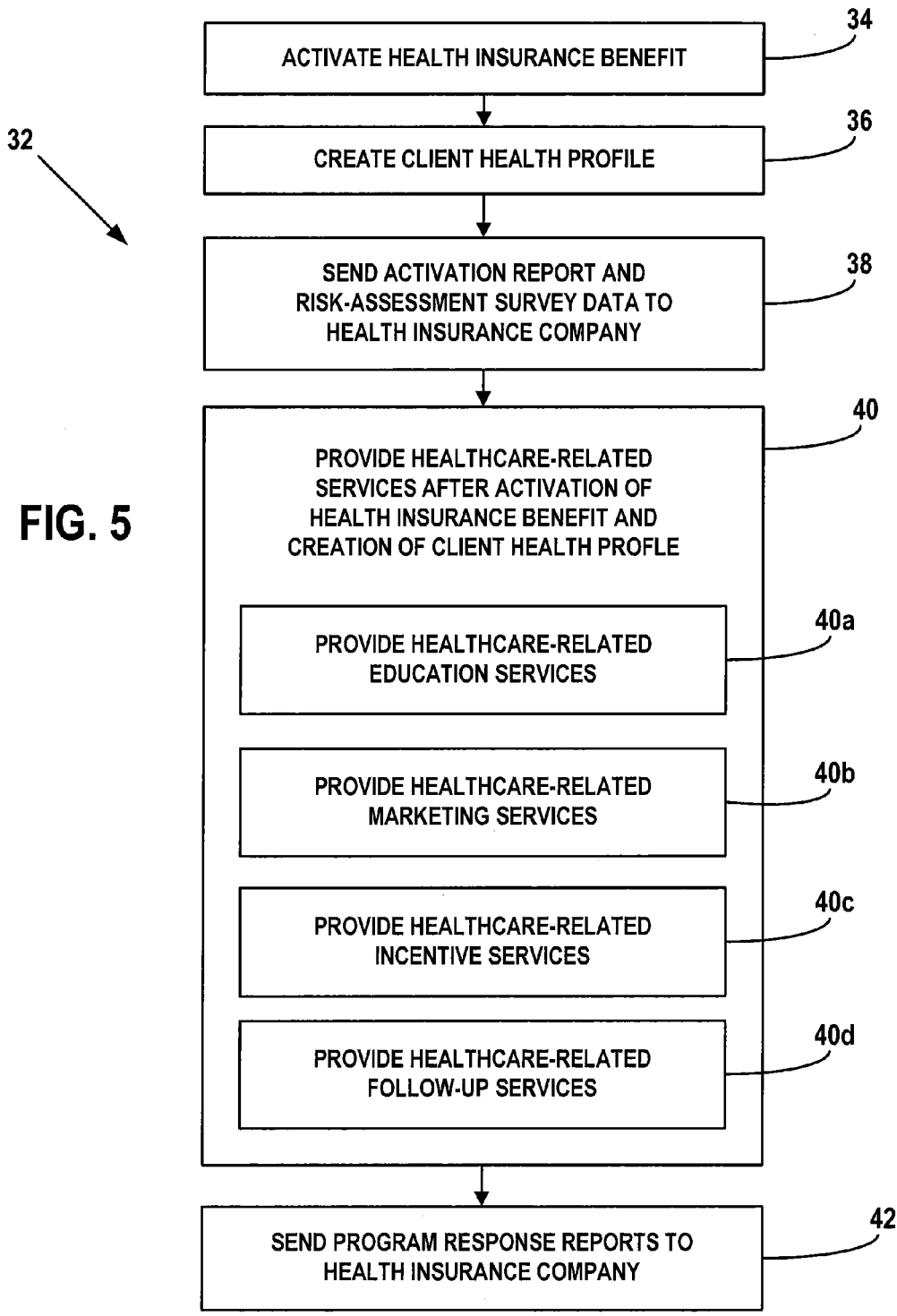
FIG. 5 is a flow chart illustration of a method of operating the system of FIGS. 1, 2, 3A and 3B according to an exemplary embodiment, the method including activating a health insurance benefit.

In an exemplary embodiment, as illustrated in FIG. 5 with continuing reference to FIGS. 1, 2, 3A, 3B and 4, a method 32 of operating the system 10 includes activating a health insurance benefit provided by the health insurance company 26 in step 34, creating a health profile of the client 28 in step 36, sending an activation report and risk-assessment survey data to the health insurance company 26 in step 38, providing healthcare-related services in step 40, and sending one or more program response reports to the health insurance company 26 in step 42. Providing healthcare-related services in the step 40 includes providing healthcare-related education services in step 40*a*, providing healthcare-related marketing services in step 40*b*, providing healthcare-related incentive services in step 40*c*, and providing healthcare-related follow-up services in step 40*d*.

Figure 6:
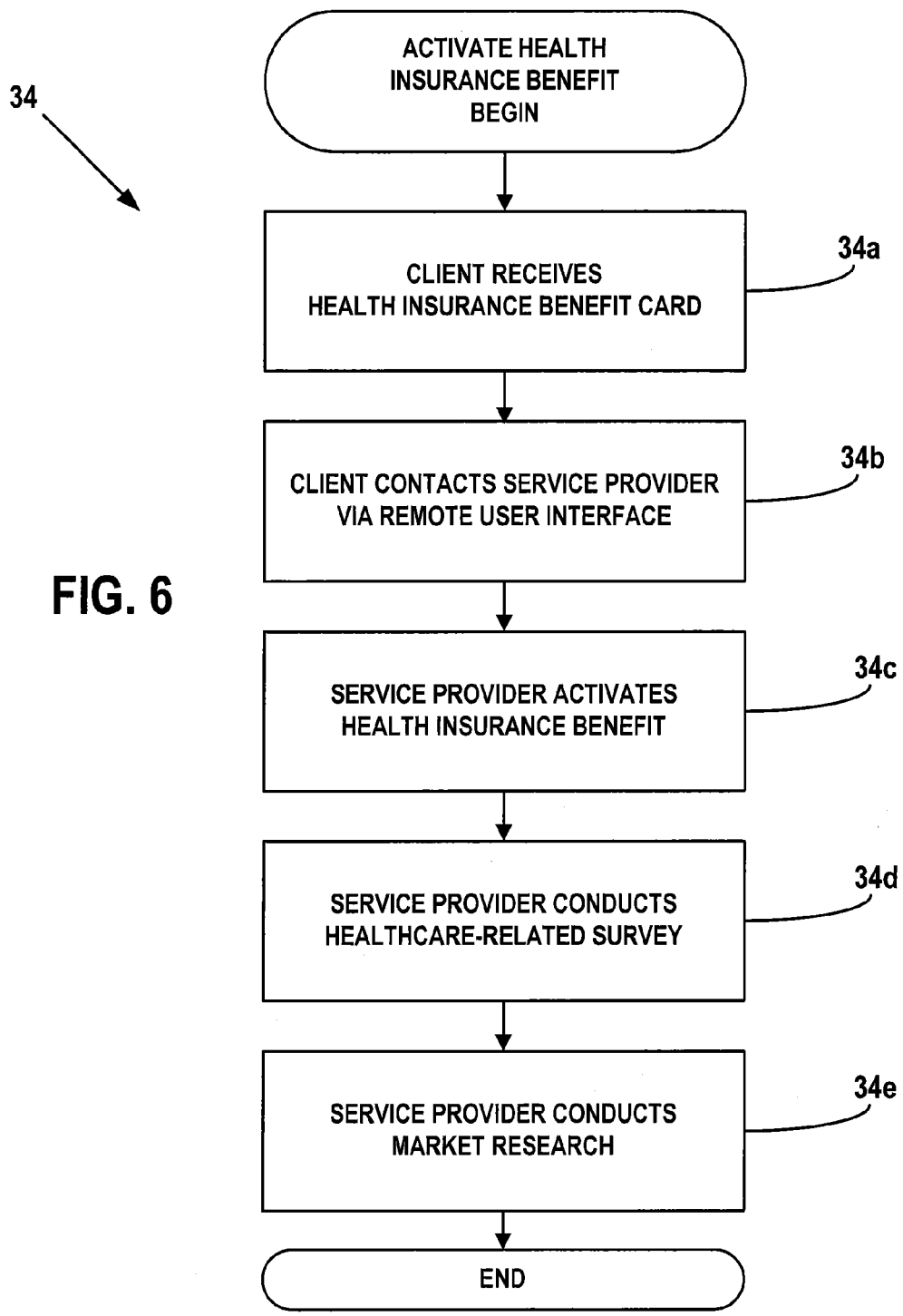
FIG. 6 is a flow chart illustration of the step of activating the health insurance benefit of FIG. 5 according to an exemplary embodiment, the step of activating the health insurance benefit including the service provider of FIG. 4 activating the health insurance benefit.

In an exemplary embodiment, as illustrated in FIG. 6 with continuing reference to FIGS. 1, 2, 3A, 3B, 4 and 5, to activate the health insurance benefit in the step 34 of the method 32, the client 28 receives the health insurance benefit card 24*a* in step 34*a*. In an exemplary embodiment, the client 28 receives the benefit card 24*a* illustrated in either FIG. 3A or FIG. 3B via a postal service. The client 28 reads the instructions on the label 24*ab* and understands that he or she must act affirmatively in order to activate the health insurance benefit. As a result, in step 34*b*, and at the convenience of the client 28, the client 28 contacts the service provider 30 via the remote user interface 20*a* and the network 22, and thereby initiates communication with the appropriate benefit specialist employed by the service provider 30.

In an exemplary embodiment, the remote user interface 20*a* is a telephone and, in the step 34*b*, the client 28 calls the service provider 30 via the network 22. The computer 12 receives the telephone call from the client 28 and routes the telephone call to the appropriate benefit specialist employed by the service provider 30, who then speaks to the client 28 over the telephone.

In an exemplary embodiment, the remote user interface 20*a* is a computer and, in the step 34*b*, the client 28 sends an e-mail message to the service provider 30 via the network 22. The computer 12 receives the e-mail message from the client 28 and routes the e-mail message to an appropriate benefit specialist employed by the service provider 30, who then communicates with the client 28 via, for example, return e-mail and/or an immediate telephone call to the client 28.

In an exemplary embodiment, the remote user interface 20*a* is a computer and, in the step 34*b*, the client 28 accesses via the network 22 a website operated by the service provider 30 and hosted by the computer 12, and follows the instructions on the website to contact the service provider 30. In several exemplary embodiments, the client 28 contacts the service provider 30 over the website in the step 34*b* by sending an e-mail message, and/or initiating an on-line chat session, initiating a video conference over the website, initiating voice communication using, for example, Voice over Internet Protocol (VoIP), before, during or after which the computer 12 routes the communication from the client 28 to the appropriate benefit specialist employed by the service provider 30, who then communicates with the client 28.

In an exemplary embodiment, before, during or after the communication between the client 28 and the benefit specialist employed by the service provider 30, the service provider 30 activates the client 28's health insurance benefit in step 34*c* of the step 34 of the method 32, the service provider 30 conducts a healthcare-related survey with the client 28 in step 34*d*, and the service provider 30 conducts market research with the client 28 in step 34*e*.

Figure 7:
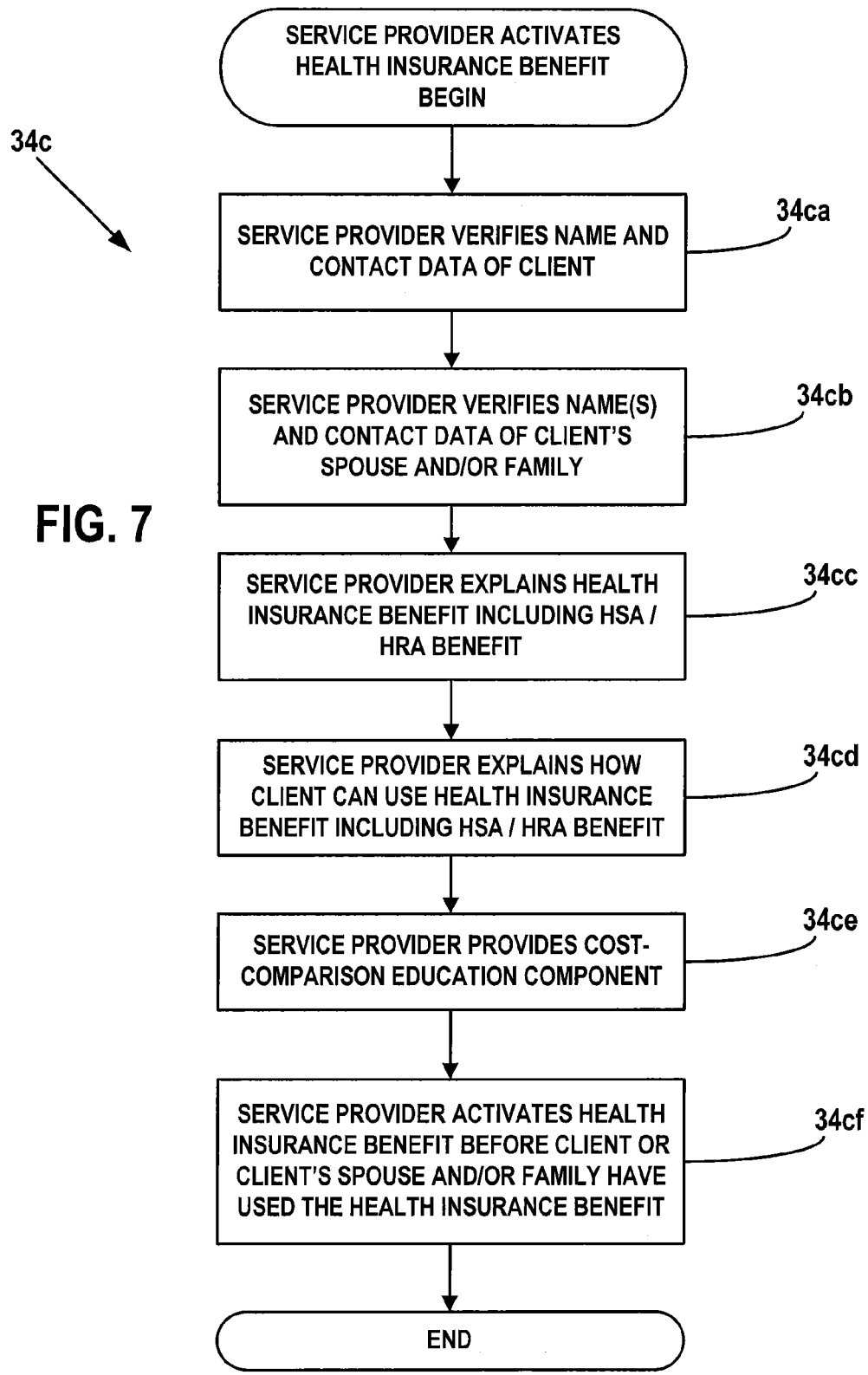
FIG. 7 is a flow chart illustration of the step of the service provider activating the health insurance benefit of FIG. 6 according to an exemplary embodiment.

In an exemplary embodiment, as illustrated in FIG. 7 with continuing reference to FIGS. 1, 2, 3A, 3B, 4, 5 and 6, for the service provider 30 to activate the client 28's health insurance benefit in the step 34*c* of the step 34 of the method 32, the benefit specialist of the service provider 30 communicates with the client 28 in step 34*ca* to verify the client 28's name, correct spelling of name, spouse's name, dependents' names, residence address, post office address, home telephone number, work telephone number, facsimile number, home or personal e-mail address, work e-mail address, and/or any combination thereof. The benefit specialist of the service provider 30 can then input the data verified in the step 34*ca* into the name and contact data 18*a* of the client data 18 in the database 16, which is stored in the computer readable medium 14, and/or revise the data already stored in the name and contact data 18*a*.

Before, during or after the step 34*ca*, the benefit specialist of the service provider 30 communicates with the client 28 in step 34*cb* to verify the names and contact data for the spouse and/or family members or dependents of the client 28 who are also entitled to a health insurance benefit provided by the health insurance company 26, including the name, correct spelling of name, residence address, post office address, home telephone number, work telephone number, facsimile number, home or personal e-mail address, work e-mail address, and/or any combination thereof, for each of the client 28's spouse and family members or dependents. The benefit specialist of the service provider 30 then inputs the data verified in the step 34*cb* into the name and contact data 18*a* of the client data 18 in the database 16, which is stored in the computer readable medium 14, and/or revises the data already stored in the name and contact data 18*a*.

Before, during or after the steps 34*cc* and 34*cb*, the benefit specialist of the service provider 30 then explains the client 28's health insurance benefit, including the client 28's Health Savings Account (HSA) and Health Reimbursement Account (HRA) benefit, in step 34*cc*. During the step 34*cc*, the benefit specialist of the service provider 30 explains the health insurance benefit to the client 28, including explaining the existence of all available plans, including any and all medical, dental, prescription drug, passive dental and vision plans, and explaining deductibles, co-pays, out-of-pocket minimums and out-of-pocket maximums. The benefit specialist of the service provider 30 then explains in step 34*cd* how the client 28 can use the health insurance benefit explained in the step 34*cc*.

Before, during or after the steps 34*cc* and 34*cd*, the benefit specialist of the service provider 30 provides a cost-comparison education component in step 34*ce*. More particularly, the benefit specialist of the service provider 30 provides information as to less-expensive outlets for healthcare-related goods and/or services based on, for example, the geographic location of the client 28. In an exemplary embodiment, in the step 34*ce*, the benefit specialist of the service provider 30 may inform the client 28 as to preferential or reduced pricing on certain prescription drugs, which are available at certain retailers located near the residence address and/or work address of the client 28.

In step 34*cf*, the benefit specialist of the service provider 30 activates the health insurance benefit for the client 28, in accordance with any further procedures required by the health insurance company 26. As a result, the health insurance benefit provided by the health insurance company 26 to the client 28 is activated after the client 28 has been educated as to the health insurance benefit, and as to how to use the health insurance benefit. Since the client 28 is now educated with respect to his or her health insurance benefit, the likelihood of unnecessary claims, and/or any confusion regarding the health insurance benefit, is reduced. Moreover, the quantity of subsequent customer-care telephone calls or messages to the health insurance company 26, any related broker, the employer of the client 28, and/or any related third party administrator (TPA), is reduced.

In an exemplary embodiment, the step 34*c* of the step 34 of the method 32 requires about four (4) minutes of communication between the client 28 and the benefit specialist of the service provider 30.

In an exemplary embodiment, with continuing reference to FIGS. 1-7, for the service provider 30 to conduct a healthcare-related survey in the step 34*d* (FIG. 6) of the step 34 of the method 32, the benefit specialist of the service provider 30 determines health-related indicators, risk factors, and/or healthcare goals specific to the client 28, such as, for example, seat belt use, diet, exercise, prescription drug use, and/or any combination thereof. In an exemplary embodiment, the data collected in the step 34*d* is stored in one or more of the healthcare-needs data 18*b*, the lifestyle survey data 18*c*, and/or the risk-assessment survey data 18*d*, in the client data 18 in the database 16 stored in the computer readable medium 14. In an exemplary embodiment, the step 34*d* of the step 34 of the method 32 requires about four (4) minutes of communication between the client 28 and the benefit specialist of the service provider 30.

In an exemplary embodiment, for the service provider 30 to conduct market research in the step 34*e* (FIG. 6) of the step 34 of the method 32, the benefit specialist of the service provider 30 collects customized market research data based on a survey provided by the health insurance company 26. In an exemplary embodiment, the data collected in the step 34*e* is stored in one or more of the healthcare-needs data 18*b*, the lifestyle survey data 18*c*, and/or the risk-assessment survey data 18*d*, in the client data 18 in the database 16 stored in the computer readable medium 14. In an exemplary embodiment, the step 34*e* of the step 34 of the method 32 requires about two (2) minutes of communication between the client 28 and the benefit specialist of the service provider 30. After the step 34*e* of the step 34 of the method 32 is completed, the conversation or communication between the client 28 and the benefit specialist of the service provider 30 ends.

In an exemplary embodiment, before, during and/or after the step 34 of the method 32, the client health profile is created in the step 36 (FIG. 5) of the method 32, as noted above. The client health profile created in the step 36 includes the data collected in the steps 34*ca*, 34*cb*, 34*d* and/or 34*e* in whole or in part, and/or the data stored in the name and contact data 18*a*, the healthcare needs data 18*b*, the lifestyle survey data 18*c*, and/or the risk-assessment survey data 18*d* in whole or in part, and/or any combination thereof.

In an exemplary embodiment, an activation report and risk-assessment survey data is sent by the service provider 30 to the health insurance company 26 in the step 38 (FIG. 5) of the method 32, as noted above. In an exemplary embodiment, the risk-assessment survey data sent to the health insurance company 26 in the step 38 is based on, and/or includes, the data in the client health profile created in the step 36 in whole or in part, and thus is at least partially dependent upon the client health profile created in the step 36. In an exemplary embodiment, the risk-assessment survey data sent to the health insurance company 26 in the step 38 includes the data in the client health profile created in the step 36 in whole or in part, and data in other client health profiles created for additional clients 28 in whole or in part, and thus is at least partially dependent upon the client health profile created in the step 36. In an exemplary embodiment, the risk-assessment survey data is provided to the health insurance company 26 in the step 38 for "predictive modeling" purposes, offering significant insight into future risk for the health insurance company 26, enabling the health insurance company 26 to optimize its models based on actual member or client data rather than on past claims or general market data, permitting the health insurance company 26 to assess customer satisfaction and current and future program adoption rates, and/or permitting the health insurance company 26 to gather valuable market research directly from existing customers or clients. The risk-assessment survey data in the client health profile provided back to the health insurance company 26 in the step 38 may include data on diet, exercise, health issues, family history, eating and smoking habits, symptoms, seat-belt usage, and/or other risk factors that may contribute to higher health care premiums. In an exemplary embodiment, the activation report provided to the health insurance company 26 in the step 38 is provided monthly, and demonstrates a high success rate in generating member or client response, educating the clients 28 on benefits, and delivering messaging from the company 26 to the clients 28.

In an exemplary embodiment, if the client 28 has a spouse, then the spouse of the client 28 receives the health insurance benefit card 24b, activates his or her own health insurance benefit, and is introduced and/or educated with respect to his or her health insurance benefit provided by the health insurance company 26, in accordance with the foregoing, including the above-described steps 34, 36 and 38. In an exemplary embodiment, during the step 34, the spouse of the client 28 (who is another client 28) communicates with an appropriate benefit specialist employed by the service provider 30 via the network 22 and the remote user interfaces 20b, in accordance with the foregoing, including the above-described steps 34, 36 and 38.

In an exemplary embodiment, with continuing reference to FIGS. 1-7, to provide healthcare-related education services to the client 28 in the step 40a (FIG. 5), the service provider 30 sends quarterly newsletters updating the client 28 about benefits, generic drugs, over-the-counter (OTC) equivalent drugs, and other drug substitutes. In an exemplary embodiment, to provide healthcare-related education services to the client 28 in the step 40a (FIG. 5), the service provider 30 provides education regarding the Top 10 questions the client 28 should ask his or her doctor, and/or the Top 10 Health Tips based on seasonal appropriateness (flu-related tips in the winter, allergy-related tips in the spring, etc.), stress-management advice, healthy eating habits, and diet. To carry out the step 40a, the health-related educational services may be delivered via the network 22, via a postal service, and/or any combination thereof.

In an exemplary embodiment, to provide healthcare-related educational services to the client 28 in the step 40a (FIG. 5), the service provider 30 targets specific disease prevention and health management education programs for conditions specific to the client 28, or for which the client 28 is at risk, such as, for example, high blood pressure, obesity, diabetes, etc., with the goal of preventing the top 80% of the clients 28 of the health insurance company 26, who do not have to fight diseases, from falling into the bottom 20% of the health insurance company 26, who do have to fight diseases, thereby lowering the expenses of the health insurance company 26. The provision of healthcare-related educational services in the step 40a may be based on, or at least partially dependent upon, the health profile of the client 28 created in the step 36 of the method 32, and thus the educational services provided in the step 40a are specific to the client 28.

In an exemplary embodiment, to provide healthcare-related marketing services in the step 40b (FIG. 5), the service provider 30 provides brand-loyalty programs, distributing relevant and specific health-related gifts to the client 28 as appropriate with the targeted educational messaging discussed in the step 40a. For example, to carry out the steps 40a and 40b, for "Skin Cancer Month," the service provider 30 sends educational material to the client 28 discussing skin cancer and the cessation of smoking in the step 40a, and sends nicotine patch samples therewith in the step 40b.

In an exemplary embodiment, to provide healthcare-related marketing services in the step 40b, the service provider 30 provides relevant, chosen gifts to the client 28 to increase brand loyalty and drive repeat business. The gifts provided in the step 40b may be based on, or at least partially dependent upon, the client profile created in the step 36, the data collected in the steps 34ca, 34cb, 34d and/or 34e in whole or in part, and/or the data stored in the name and contact data 18a, the healthcare needs data 18b, the lifestyle survey data 18c, and/or the risk-assessment survey data 18d in whole or in part, and/or any combination thereof, and thus are specific to the client 28. As a result, the gifts provided in the step 40b may include one or more of the following: pedometers for the exercise enthusiast, first-aid kits for the car or home, recipe books, 7-day vitamin/drug dispenser-and-clock combinations, all of which are health-driven items.

In an exemplary embodiment, to provide healthcare-related incentive services in the step 40c (FIG. 5), the service provider 30 provides website incentives, gaining opt-in permission from the client 28 for e-mail communication and e-letter updates, and providing links to the health insurance company 26's website at which e-coupons can be redeemed for different goods and/services, such as, for example, workout videos, hot/cold packs, iTunes, Nefflix, etc.

In an exemplary embodiment, to provide healthcare-related incentive services in the step 40c, the service provider 30 provides incentives to the client 28 in the form of generic drug coupons, OTC coupons and samples to encourage the client 28 to use lower-cost alternatives to brand-name drugs.

In an exemplary embodiment, to provide healthcare-related follow-up services in the step 40d (FIG. 5), the service provider 30 makes a mid-year "healthy habits" call, communicating with the client 28 over the remote user interface 20a or 20b, which is in the form of a telephone, and reinforcing key consumer messages, such as, for example, the message of "just ask" for generic drugs as opposed to brand-name drugs, that is, requesting prescriptions for generic drugs instead of passively accepting prescriptions for brand-name drugs. In an exemplary embodiment, during the step 40d, the service provider 30 takes the opportunity to, for example, determine any health-status changes, monitor the progress of current programs, and redirect the client 28 to online insurance resources, and/or any combination thereof.

In an exemplary embodiment, to send program response reports to the health insurance company 26 in the step 42 (FIG. 5), the service provider 30 delivers customized survey results, year-over-year improvement trend reports from the clients 28 participating in assessment surveys, and/or year-end effectiveness and consumer behavior reports demonstrating improved health awareness and decision making among the clients 28.

In an exemplary embodiment, as a result of the execution of the method 32, the client's health insurance benefit card 24a is activated, the client 28's spouse's health insurance benefit card 24b is activated, the client 28 and his or her spouse are educated, risky behaviors and/or symptoms of the client 28 and his or her spouse are recognized, disease is more likely to be prevented, the client 28 and his or her spouse are motivated to have better health and live healthier lifestyles, the costs borne by the health insurance company 26 are more likely to be decreased, and the products offered, and the premiums charged, by the health insurance company 26 are more likely to be optimized.

In an exemplary embodiment, as a result of the execution of the method 32, the client 28 understands the health insurance benefit available to him or her, and the costs associated therewith, thereby increasing the likelihood that the client 28 will utilize the health insurance benefit correctly and become a more discerning healthcare consumer. Moreover, the number of follow-up, customer-care calls by the client 28 to the health insurance company 26, any third-party administrators, and/or any employer human resources departments, will decrease, thereby decreasing unnecessary and excessive claim reimbursement costs, and decreasing employee confusion.

In several exemplary embodiments, as illustrated in FIG. 8, a table outlining the services, benefits, results, offerings and measurements of the system 10, and/or the method 32, is generally referred to by the reference numeral 44.

In an exemplary embodiment, as illustrated in FIG. 9, a table outlining packages and programs available using the system 10, and/or the method 32, is generally referred to by the reference numeral 46. As shown in the table 46, in an exemplary embodiment, the service provider 30 depends on a revenue model based on cost per adult insured member per month, which cost is paid by the health insurance company 26 to the service provider 30. In an exemplary embodiment, three (3) revenue models are available: a first cost per adult insured client per month; a second cost per adult insured client per month, the second cost being greater than the first cost; and a third cost per adult insured client per month, the third cost being greater than the second cost; in an exemplary embodiment, the first, second and third costs are $2, $3 and $4, respectively. In several exemplary embodiments, instead of, or in addition to respective costs of $2, $3 and $4, a wide range of costs, and/or increments therebetween, may be used for the revenue models. In several exemplary embodiments, the quantity of revenue models may range from one to an unlimited number. In an exemplary embodiment, the type and quantity of the services provided during the execution of the method 32 vary with respect to which revenue model is selected by the health insurance company 26; in an exemplary embodiment, the quantity of services provided increases as the cost per adult insured client per month increases. In an exemplary embodiment, the $4 per adult insured client per month revenue model includes all of the services outlined in the table 46. In an exemplary embodiment, some of the services outlined in the table 46 are omitted from the $3 per adult insured client per month revenue model. In an exemplary embodiment, some of the services outlined in the table 46 are omitted from the $2 per adult insured client per month revenue model, in addition to the services omitted in the $3 per adult insured client per month revenue model.

In an exemplary embodiment, the remote user interfaces 20a and 20b, and/or the computer 12, may be characterized as a thick client. In an exemplary embodiment, the remote user interfaces 20a and 20b, and/or the computer 12, may be characterized as a thin client, and therefore the functions and/or uses of one of the remote user interfaces 20a and 20b and the computer 12 may instead be functions and/or uses of another of the remote user interfaces 20a and 20b and the computer 12. In several exemplary embodiments, the remote user interfaces 20a and 20b, and/or the computer 12, may function as both a thin client and a thick client.

Figure 10:
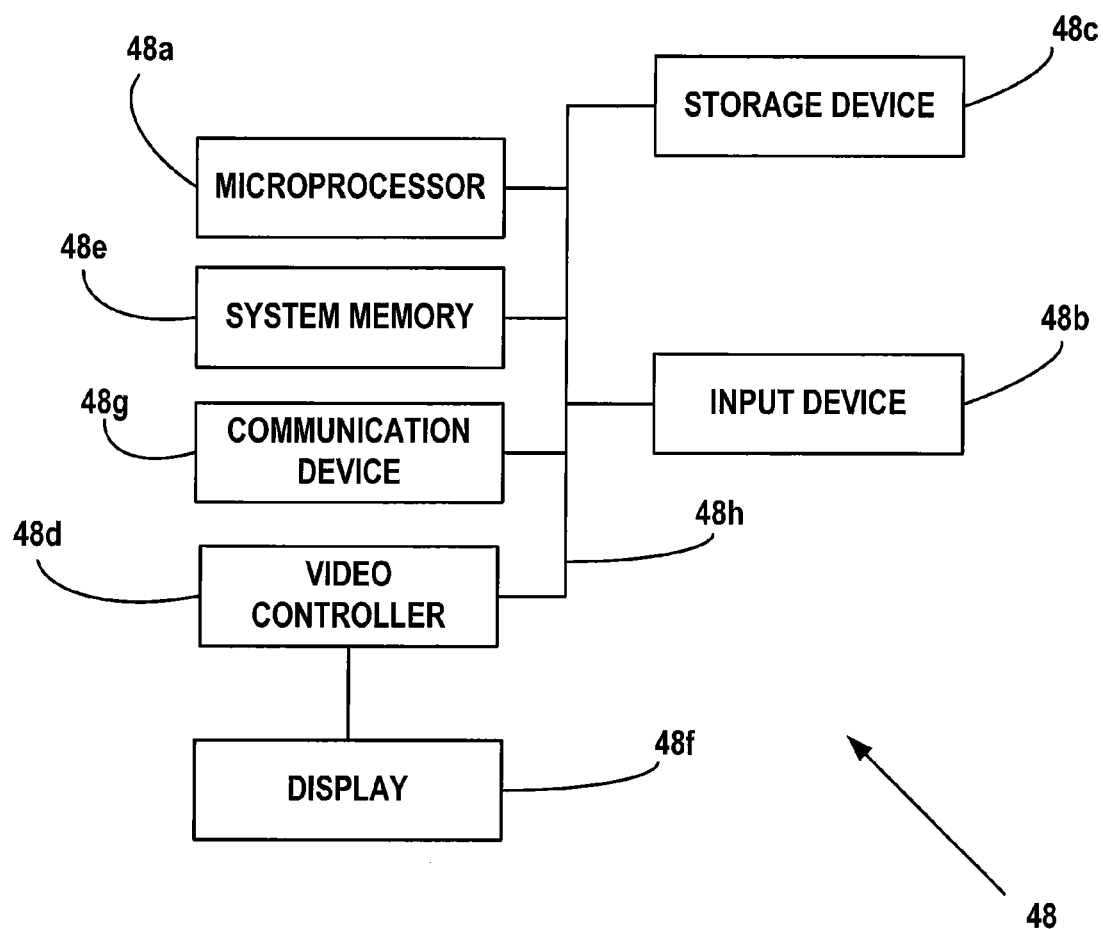
FIG. 10 is a diagrammatic illustration of a node for implementing one or more exemplary embodiments of the present disclosure.

In an exemplary embodiment, as illustrated in FIG. 10 with continuing reference to FIGS. 1, 2, 3A, 3B, 4, 5, 6, 7, 8 and 9, an illustrative node 48 for implementing one or more embodiments of one or more of the above-described networks, elements, methods and/or steps, and/or any combination thereof, is depicted. The node 48 includes a microprocessor 48a, an input device 48b, a storage device 48c, a video controller 48d, a system memory 48e, a display 48f, and a communication device 48g, all of which are interconnected by one or more buses 48h. In several exemplary embodiments, the storage device 48c may include a floppy drive, hard drive, CD-ROM, optical drive, any other form of storage device and/or any combination thereof. In several exemplary embodiments, the storage device 48c may include, and/or be capable of receiving, a floppy disk, CD-ROM, DVD-ROM, or any other form of computer readable medium that may contain executable instructions. In several exemplary embodiments, the communication device 48g may include a modem, network card, or any other device to enable the node to communicate with other nodes. In several exemplary embodiments, any node represents a plurality of interconnected (whether by intranet or Internet) computer systems, including without limitation, personal computers, mainframes, PDAs, and cellular telephones.

In several exemplary embodiments, at least one of the computer 12, the network 22, the remote user interfaces 20a and 20b, the computer readable medium 14 and the database 16, is, or at least includes, the node 48 and/or components thereof, and/or one or more nodes that are substantially similar to the node 48 and/or components thereof.

In several exemplary embodiments, a computer system typically includes at least hardware capable of executing machine readable instructions, as well as the software for executing acts (typically machine-readable instructions) that produce a desired result. In several exemplary embodiments, a computer system may include hybrids of hardware and software, as well as computer sub-systems.

In several exemplary embodiments, hardware generally includes at least processor-capable platforms, such as client-machines (also known as personal computers or servers), and hand-held processing devices (such as smart phones, personal digital assistants (PDAs), or personal computing devices (PCDs), for example). In several exemplary embodiments, hardware may include any physical device that is capable of storing machine-readable instructions, such as memory or other data storage devices. In several exemplary embodiments, other forms of hardware include hardware sub-systems, including transfer devices such as modems, modem cards, ports, and port cards, for example.

In several exemplary embodiments, software includes any machine code stored in any memory medium, such as RAM or ROM, and machine code stored on other devices (such as floppy disks, flash memory, or a CD ROM, for example). In several exemplary embodiments, software may include source or object code. In several exemplary embodiments, software encompasses any set of instructions capable of being executed on a node such as, for example, on a client machine or server.

In several exemplary embodiments, combinations of software and hardware could also be used for providing enhanced functionality and performance for certain embodiments of the present disclosure. In an exemplary embodiment, software functions may be directly manufactured into a silicon chip. Accordingly, it should be understood that combinations of hardware and software are also included within the definition of a computer system and are thus envisioned by the present disclosure as possible equivalent structures and equivalent methods.

In several exemplary embodiments, computer readable mediums include, for example, passive data storage, such as a random access memory (RAM) as well as semi-permanent data storage such as a compact disk read only memory (CD-ROM). One or more exemplary embodiments of the present disclosure may be embodied in the RAM of a computer to transform a standard computer into a new specific computing machine.

In several exemplary embodiments, data structures are defined organizations of data that may enable an embodiment of the present disclosure. In an exemplary embodiment, a data structure may provide an organization of data, or an organization of executable code. In several exemplary embodiments, data signals could be carried across transmission mediums and store and transport various data structures, and, thus, may be used to transport an embodiment of the present disclosure.

In several exemplary embodiments, the network 22, and/or one or more portions thereof, may be designed to work on any specific architecture. In an exemplary embodiment, one or more portions of the network 22 may be executed on a single computer, local area networks, client-server networks, wide area networks, internets, hand-held and other portable and wireless devices and networks.

In several exemplary embodiments, a database may be any standard or proprietary database software, such as Oracle, Microsoft Access, SyBase, or DBase II, for example. In several exemplary embodiments, the database may have fields, records, data, and other database elements that may be associated through database specific software. In several exemplary embodiments, data may be mapped. In several exemplary embodiments, mapping is the process of associating one data entry with another data entry. In an exemplary embodiment, the data contained in the location of a character file can be mapped to a field in a second table. In several exemplary embodiments, the physical location of the database is not limiting, and the database may be distributed. In an exemplary embodiment, the database may exist remotely from the server, and run on a separate platform. In an exemplary embodiment, the database may be accessible across the Internet. In several exemplary embodiments, more than one database may be implemented.

In several exemplary embodiments, while different steps, processes, and procedures are described as appearing as distinct acts, one or more of the steps, one or more of the processes, and/or one or more of the procedures could also be performed in different orders, simultaneously and/or sequentially. In several exemplary embodiments, the steps, processes and/or procedures could be merged into one or more steps, processes and/or procedures.

A method has been described that includes providing a health insurance benefit card to a client of a health insurance company, the health insurance benefit card evidencing a health insurance benefit for the client; directing the client to take an affirmative action to activate the health insurance benefit evidenced by the health insurance benefit card; and activating the health insurance benefit evidenced by the health insurance benefit card in response to the affirmative action taken by the client. In an exemplary embodiment, activating the health insurance benefit evidenced by the health insurance benefit card in response to the affirmative action taken by the client comprises verifying name and contact data specific to the client; explaining the health insurance benefit to the client; explaining to the client how the client can use the health insurance benefit; and activating the health insurance benefit before the client has used the health insurance benefit. In an exemplary embodiment, the affirmative action comprises initiation of communication by the client; and wherein verifying name and contact data specific to the client, explaining the health insurance benefit to the client, explaining how the client can use the health insurance benefit, and activating the health insurance benefit before the client has used the health insurance benefit, occurs during the communication initiated by the client. In an exemplary embodiment, the initiation of communication comprises one or more of the following: a telephone call by the client; an e-mail message from the client; and a website access by the client. In an exemplary embodiment, the method comprises conducting a healthcare-related survey with the client during the communication initiated by the client; and creating a client health profile specific to the client in response to conducting the healthcare-related survey. In an exemplary embodiment, the method comprises providing healthcare-related services after activating the health insurance benefit evidenced by the health insurance benefit card, comprising one or more of the following: providing healthcare-related education services to the client; providing healthcare-related marketing services; providing healthcare-related incentive services; and providing healthcare-related follow-up services with the client; wherein one or more of the education, marketing, incentive and follow-up services are at least partially dependent upon the client health profile and thus are specific to the client. In an exemplary embodiment, the method comprises one or more of the following: sending risk-assessment survey data to the health insurance company, the risk-assessment data being at least partially dependent upon the client health profile; and sending one or more program response reports to the health insurance company. In an exemplary embodiment, the health insurance benefit card comprises a wallet-sized card; and a peel-off label coupled to the wallet-sized card, the peel-off label comprising one or more instructional messages to the client, the one or more instructional messages comprising an instructional message directing the client to take the affirmative action to activate the health insurance benefit evidenced by the health insurance benefit card. In an exemplary embodiment, the instructional message directing the client to take the affirmative action to activate the health insurance benefit evidenced by the health insurance benefit card comprises an instructional message directing the client to use a remote user interface to take the affirmative action to activate the health insurance benefit evidenced by the health insurance benefit card, the remote user interface comprising at least one of a telephone and a computer; and wherein the affirmative action comprises one or more of the following: using the telephone to call a telephone number; using the computer to send an e-mail message; and using the computer to access a website. In an exemplary embodiment, activating the health insurance benefit evidenced by the health insurance benefit card in response to the affirmative action taken by the client comprises verifying name and contact data specific to the client; explaining the health insurance benefit to the client; explaining to the client how the client can use the health insurance benefit; and activating the health insurance benefit before the client has used the health insurance benefit; wherein the affirmative action comprises initiation of communication by the client, the initiation of communication comprising one or more of the following: a telephone call by the client, an e-mail message from the client, and a website access by the client; wherein verifying name and contact data specific to the client, explaining the health insurance benefit to the client, explaining how the client can use the health insurance benefit, and activating the health insurance benefit before the client has used the health insurance benefit, occurs during the communication initiated by the client; wherein the method further comprises conducting a healthcare-related survey with the client during the communication initiated by the client; creating a client health profile specific to the client in response to conducting the healthcare-related survey; sending risk-assessment survey data to the health insurance company, the risk-assessment data being at least partially dependent upon the client health profile; providing healthcare-related services after activating the health insurance benefit evidenced by the health insurance benefit card, comprising one or more of the following: providing healthcare-related education services to the client; providing healthcare-related marketing services; providing healthcare-related incentive services; and providing healthcare-related follow-up services with the client; and sending one or more program response reports to the health insurance company; wherein one or more of the education, marketing, incentive and follow-up services are at least partially dependent upon the client health profile and thus are specific to the client; and wherein the health insurance benefit card comprises a wallet-sized card; and a peel-off label coupled to the wallet-sized card, the peel-off label comprising one or more instructional messages to the client, the one or more instructional messages comprising an instructional message directing the client to use a remote user interface to take the affirmative action to activate the health insurance benefit evidenced by the health insurance benefit card, the remote user interface comprising at least one of a telephone and a computer.

A computer readable medium has been described that includes a plurality of instructions stored therein, the plurality of instructions comprising instructions for providing a health insurance benefit card to a client of a health insurance company, the health insurance benefit card evidencing a health insurance benefit for the client; instructions for directing the client to take an affirmative action to activate the health insurance benefit evidenced by the health insurance benefit card; and instructions for activating the health insurance benefit evidenced by the health insurance benefit card in response to the affirmative action taken by the client. In an exemplary embodiment, instructions for activating the health insurance benefit evidenced by the health insurance benefit card in response to the affirmative action taken by the client comprises instructions for verifying name and contact data specific to the client; instructions for explaining the health insurance benefit to the client; instructions for explaining to the client how the client can use the health insurance benefit; and instructions for activating the health insurance benefit before the client has used the health insurance benefit. In an exemplary embodiment, the affirmative action comprises initiation of communication by the client; and wherein verifying name and contact data specific to the client, explaining the health insurance benefit to the client, explaining how the client can use the health insurance benefit, and activating the health insurance benefit before the client has used the health insurance benefit, occurs during the communication initiated by the client. In an exemplary embodiment, the initiation of communication comprises one or more of the following: a telephone call by the client; an e-mail message from the client; and a website access by the client. In an exemplary embodiment, the plurality of instructions comprises instructions for conducting a healthcare-related survey with the client during the communication initiated by the client; and instructions for creating a client health profile specific to the client in response to conducting the healthcare-related survey. In an exemplary embodiment, the plurality of instructions comprises instructions for providing healthcare-related services after activating the health insurance benefit evidenced by the health insurance benefit card, comprising one or more of the following: instructions for providing healthcare-related education services to the client; instructions for providing healthcare-related marketing services; instructions for providing healthcare-related incentive services; and instructions for providing healthcare-related follow-up services with the client; wherein one or more of the education, marketing, incentive and follow-up services are at least partially dependent upon the client health profile and thus are specific to the client. In an exemplary embodiment, the plurality of instructions comprises one or more of the following: instructions for sending risk-assessment survey data to the health insurance company, the risk-assessment data being at least partially dependent upon the client health profile; and instructions for sending one or more program response reports to the health insurance company. In an exemplary embodiment, the health insurance benefit card comprises a wallet-sized card; and a peel-off label coupled to the wallet-sized card, the peel-off label comprising one or more instructional messages to the client, the one or more instructional messages comprising an instructional message directing the client to take the affirmative action to activate the health insurance benefit evidenced by the health insurance benefit card. In an exemplary embodiment, the instructional message directing the client to take the affirmative action to activate the health insurance benefit evidenced by the health insurance benefit card comprises an instructional message directing the client to use a remote user interface to take the affirmative action to activate the health insurance benefit evidenced by the health insurance benefit card, the remote user interface comprising at least one of a telephone and a computer; and wherein the affirmative action comprises one or more of the following: using the telephone to call a telephone number; using the computer to send an e-mail message; and using the computer to access a website. In an exemplary embodiment, instructions for activating the health insurance benefit evidenced by the health insurance benefit card in response to the affirmative action taken by the client comprises instructions for verifying name and contact data specific to the client; instructions for explaining the health insurance benefit to the client; instructions for explaining to the client how the client can use the health insurance benefit; and instructions for activating the health insurance benefit before the client has used the health insurance benefit; wherein the affirmative action comprises initiation of communication by the client, the initiation of communication comprising one or more of the following: a telephone call by the client, an e-mail message from the client, and a website access by the client; wherein verifying name and contact data specific to the client, explaining the health insurance benefit to the client, explaining how the client can use the health insurance benefit, and activating the health insurance benefit before the client has used the health insurance benefit, occurs during the communication initiated by the client; wherein the plurality of instructions further comprises instructions for conducting a healthcare-related survey with the client during the communication initiated by the client; instructions for creating a client health profile specific to the client in response to conducting the healthcare-related survey; instructions for sending risk-assessment survey data to the health insurance company, the risk-assessment data being at least partially dependent upon the client health profile; instructions for providing healthcare-related services after activating the health insurance benefit evidenced by the health insurance benefit card, comprising one or more of the following: instructions for providing healthcare-related education services to the client; instructions for providing healthcare-related marketing services; instructions for providing healthcare-related incentive services; and instructions for providing healthcare-related follow-up services with the client; and instructions for sending one or more program response reports to the health insurance company; wherein one or more of the education, marketing, incentive and follow-up services are at least partially dependent upon the client health profile and thus are specific to the client; and wherein the health insurance benefit card comprises a wallet-sized card; and a peel-off label coupled to the wallet-sized card, the peel-off label comprising one or more instructional messages to the client, the one or more instructional messages comprising an instructional message directing the client to use a remote user interface to take the affirmative action to activate the health insurance benefit evidenced by the health insurance benefit card, the remote user interface comprising at least one of a telephone and a computer.

A system has been described that includes means for providing a health insurance benefit card to a client of a health insurance company, the health insurance benefit card evidencing a health insurance benefit for the client; means for directing the client to take an affirmative action to activate the health insurance benefit evidenced by the health insurance benefit card; and means for activating the health insurance benefit evidenced by the health insurance benefit card in response to the affirmative action taken by the client. In an exemplary embodiment, means for activating the health insurance benefit evidenced by the health insurance benefit card in response to the affirmative action taken by the client comprises means for verifying name and contact data specific to the client; means for explaining the health insurance benefit to the client; means for explaining to the client how the client can use the health insurance benefit; and means for activating the health insurance benefit before the client has used the health insurance benefit. In an exemplary embodiment, the affirmative action comprises initiation of communication by the client; and wherein verifying name and contact data specific to the client, explaining the health insurance benefit to the client, explaining how the client can use the health insurance benefit, and activating the health insurance benefit before the client has used the health insurance benefit, occurs during the communication initiated by the client. In an exemplary embodiment, the initiation of communication comprises one or more of the following: a telephone call by the client; an e-mail message from the client; and a website access by the client. In an exemplary embodiment, the system comprises means for conducting a healthcare-related survey with the client during the communication initiated by the client; and means for creating a client health profile specific to the client in response to conducting the healthcare-related survey. In an exemplary embodiment, the system comprises means for providing healthcare-related services after activating the health insurance benefit evidenced by the health insurance benefit card, comprising one or more of the following: means for providing healthcare-related education services to the client; means for providing healthcare-related marketing services; means for providing healthcare-related incentive services; and means for providing healthcare-related follow-up services with the client; wherein one or more of the education, marketing, incentive and follow-up services are at least partially dependent upon the client health profile and thus are specific to the client. In an exemplary embodiment, the system comprises one or more of the following: means for sending risk-assessment survey data to the health insurance company, the risk-assessment data being at least partially dependent upon the client health profile; and means for sending one or more program response reports to the health insurance company. In an exemplary embodiment, the health insurance benefit card comprises a wallet-sized card; and a peel-off label coupled to the wallet-sized card, the peel-off label comprising one or more instructional messages to the client, the one or more instructional messages comprising an instructional message directing the client to take the affirmative action to activate the health insurance benefit evidenced by the health insurance benefit card. In an exemplary embodiment, the instructional message directing the client to take the affirmative action to activate the health insurance benefit evidenced by the health insurance benefit card comprises an instructional message directing the client to use a remote user interface to take the affirmative action to activate the health insurance benefit evidenced by the health insurance benefit card, the remote user interface comprising at least one of a telephone and a computer; and wherein the affirmative action comprises one or more of the following: using the telephone to call a telephone number; using the computer to send an e-mail message; and using the computer to access a website.

In an exemplary embodiment, means for activating the health insurance benefit evidenced by the health insurance benefit card in response to the affirmative action taken by the client comprises means for verifying name and contact data specific to the client; means for explaining the health insurance benefit to the client; means for explaining to the client how the client can use the health insurance benefit; and means for activating the health insurance benefit before the client has used the health insurance benefit; wherein the affirmative action comprises initiation of communication by the client, the initiation of communication comprising one or more of the following: a telephone call by the client, an e-mail message from the client, and a website access by the client; wherein verifying name and contact data specific to the client, explaining the health insurance benefit to the client, explaining how the client can use the health insurance benefit, and activating the health insurance benefit before the client has used the health insurance benefit, occurs during the communication initiated by the client; wherein the system further comprises means for conducting a healthcare-related survey with the client during the communication initiated by the client; means for creating a client health profile specific to the client in response to conducting the healthcare-related survey; means for sending risk-assessment survey data to the health insurance company, the risk-assessment data being at least partially dependent upon the client health profile; means for providing healthcare-related services after activating the health insurance benefit evidenced by the health insurance benefit card, comprising one or more of the following: means for providing healthcare-related education services to the client; means for providing healthcare-related marketing services; means for providing healthcare-related incentive services; and means for providing healthcare-related follow-up services with the client; and means for sending one or more program response reports to the health insurance company; wherein one or more of the education, marketing, incentive and follow-up services are at least partially dependent upon the client health profile and thus are specific to the client; and wherein the health insurance benefit card comprises a wallet-sized card; and a peel-off label coupled to the wallet-sized card, the peel-off label comprising one or more instructional messages to the client, the one or more instructional messages comprising an instructional message directing the client to use a remote user interface to take the affirmative action to activate the health insurance benefit evidenced by the health insurance benefit card, the remote user interface comprising at least one of a telephone and a computer.

A system has been described that includes a health insurance benefit card for a client of a health insurance company, the health insurance benefit card evidencing a health insurance benefit for the client, the health insurance benefit card comprising a wallet-sized card; and a peel-off label coupled to the wallet-sized card, the peel-off label comprising one or more instructional messages to the client, the one or more instructional messages comprising an instructional message directing the client to activate the health insurance benefit evidenced by the health insurance benefit card. In an exemplary embodiment, the system comprises a remote user interface; wherein the instructional message directing the client to activate the health insurance benefit evidenced by the health insurance benefit card comprises an instructional message directing the client to use the remote user interface to activate the health insurance benefit evidenced by the health insurance benefit card. In an exemplary embodiment, the remote user interface comprises at least one of a telephone and a computer; and wherein the instructional message directing the client to use the remote user interface to activate the health insurance benefit evidenced by the health insurance benefit card comprises one or more of the following: an instructional message directing the client to call a telephone number to activate the health insurance benefit evidenced by the health insurance benefit card; an instructional message directing the client to send an e-mail message to activate the health insurance benefit evidenced by the health insurance benefit card; and an instructional message directing the client to access a website to activate the health insurance benefit evidenced by the health insurance benefit card. In an exemplary embodiment, the system comprises a computer operably coupled to the remote user interface via a network; a computer readable medium operably coupled to the computer; and a database stored in the computer readable medium, the database comprising data specific to the client, the data specific to the client comprising name and contact data; and one or more following: healthcare needs data; lifestyle survey data; and risk-assessment survey data.

It is understood that variations may be made in the foregoing without departing from the scope of the disclosure. Furthermore, the elements and teachings of the various illustrative exemplary embodiments may be combined in whole or in part in some or all of the illustrative exemplary embodiments. In addition, one or more of the elements and teachings of the various illustrative exemplary embodiments may be omitted, at least in part, and/or combined, at least in part, with one or more of the other elements and teachings of the various illustrative embodiments.

Any spatial references such as, for example, "upper," "lower," "above," "below," "between," "vertical," "horizontal," "angular," "upwards," "downwards," "side-to-side," "left-to-right," "right-to-left," "top-to-bottom," "bottom-to-top," "top," "bottom," "bottom-up," "top-down," etc., are for the purpose of illustration only and do not limit the specific orientation or location of the structure described above.

In several exemplary embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

Although several exemplary embodiments have been described in detail above, the embodiments described are exemplary only and are not limiting, and those skilled in the art will readily appreciate that many other modifications, changes and/or substitutions are possible in the exemplary embodiments without materially departing from the novel teachings and advantages of the present disclosure. Accordingly, all such modifications, changes and/or substitutions are intended to be included within the scope of this disclosure as defined in the following claims. In the claims, means-plus-function clauses are intended to cover the structures described herein as performing the recited function and not only structural equivalents, but also equivalent structures.

What is claimed is:

1. A system comprising:
   a health insurance benefit card that evidences health insurance benefits for a client, the health insurance benefit card comprising:
   a wallet-sized card;
   a peel-off label coupled to the wallet-sized card; and
   one or more instructional messages to the client, wherein the one or more instructional messages are printed on the peel-off label so that the one or more instructional messages are visible to the client, and wherein the one or more messages comprise an instructional message directing the client to initiate a communication to initially activate the health insurance benefits evidenced by the health insurance benefit card; and
   at least one computer, comprising:
   at least one processor;
   a computer readable medium operably coupled to the at least one processor; and
   a plurality of instructions stored in the computer readable medium, the plurality of instructions being accessible to, and executable by, the at least one processor; wherein the at least one processor is configured to perform the following steps:
   verifying, during the communication initiated by the client and thus after the client has received the health insurance benefit card, name and contact data specific to the client;
   explaining, during the communication initiated by the client and thus after the client has received the health insurance benefit card, the health insurance benefits to the client, wherein the health insurance benefits comprise one or more aspects of at least one plan, and wherein the least one plan is selected from the group consisting of a medical plan, a dental plan, a prescription drug plan, and a vision plan;
   explaining to the client, during the communication initiated by the client and thus after the client has received the health insurance benefit card, how the client can take advantage of the health insurance benefits before the client has ever used the at least one plan; and
   initially activating, during the communication initiated by the client and thus after the client has received the health insurance benefit card, the health insurance benefits before the client has ever used the at least one plan.

2. The system of claim 1, wherein the at least one processor is further configured to perform the following step:
   conducting, during the communication initiated by the client, a healthcare-related survey with the client, the healthcare-related survey being configured to collect survey data specific to the client, the survey data comprising at least one of the following: smoking habit data specific to the client's smoking habits;
   family history data specific to the client's family history;
   diet data specific to the client's diet;
   exercise data specific to the client's exercise;
   prescription drug use data specific to the client's prescription drug use; and
   seat belt use data specific to the client's seat belt use.

3. The system of claim 2, wherein the at least one processor is further configured to perform the following step:
   creating a client health profile specific to the client in response to conducting the healthcare-related survey with the client, the client health profile specific to the client comprising the survey data collected during the healthcare-related survey conducted with the client.

4. The system of claim 3, wherein the at least one processor is further configured to perform the following step:
   sending risk-assessment data to the health insurance company, the risk-assessment data being at least partially dependent upon the survey data collected during the healthcare-related survey conducted with the client.

5. The system of claim 3, wherein the at least one processor is further configured to perform the following step:
   providing healthcare-related services after initially activating the health insurance benefits evidenced by the health insurance benefit card, comprising one or more of the following:

providing healthcare-related education services to the client; providing healthcare-related marketing services; providing healthcare-related incentive services; and providing healthcare-related follow-up services with the client; wherein one or more of the education, marketing, incentive and follow-up services are at least partially dependent upon the client health profile and thus are specific to the client.

6. The system of claim 2, wherein the at least one processor is further configured to perform the following step:

sending one or more program response reports to the health insurance company.

\* \* \* \* \*

UNITED STATES PATENT AND TRADEMARK OFFICE
CERTIFICATE OF CORRECTION

PATENT NO. : 8,433,590 B2  Page 1 of 1
APPLICATION NO. : 13/405801
DATED : April 30, 2013
INVENTOR(S) : Daniel J. Prescott It is certified that error appears in the above-identified patent and that said Letters Patent is hereby corrected as shown below:

In the Specification

Column 5, line 23, change "34cc" to -- 34ca --.

Column 8, line 24, change "Nefflix" to -- Netflix --.

Signed and Sealed this
Tenth Day of September, 2013

Teresa Stanek Rea
*Acting Director of the United States Patent and Trademark Office*